United States Patent [19]

Saulietis

[11] Patent Number: 5,367,401
[45] Date of Patent: Nov. 22, 1994

[54] MICROSCOPE SLIDE ROTARY STAGE

[75] Inventor: Indulis Saulietis, Santa Fe, Tex.

[73] Assignee: Perceptive Scientific Instruments, Inc., League City, Tex.

[21] Appl. No.: 980,530

[22] Filed: Nov. 23, 1990

[51] Int. Cl.$^5$ .......................... G02B 21/34; G01N 1/10
[52] U.S. Cl. .................................. 359/398; 359/393; 359/391; 356/246
[58] Field of Search ................ 359/368, 369, 391–398, 359/900; 422/55–64, 99–104; 435/292–299; 356/244, 246

[56] References Cited

U.S. PATENT DOCUMENTS

| | | | |
|---|---|---|---|
| 588,689 | 8/1897 | Bausch | 359/393 |
| 1,713,412 | 5/1929 | Winkel | 359/394 |
| 2,265,182 | 12/1941 | Mestre | 359/394 |
| 2,500,604 | 3/1950 | Daniel | 359/391 |
| 2,656,760 | 10/1953 | Bowerman | 359/391 |
| 2,857,809 | 10/1958 | Musser et al. | 359/391 |
| 2,960,913 | 11/1960 | Herrala | 359/382 |
| 3,359,055 | 12/1967 | Krause | 359/396 |
| 3,625,586 | 12/1971 | Oleka | 359/393 |
| 3,762,798 | 10/1973 | Grubb et al. | 359/394 |
| 3,951,512 | 4/1976 | Tolles | 359/391 |
| 4,122,518 | 10/1978 | Castleman et al. | 364/413.02 |
| 4,407,570 | 10/1983 | Hayasaka | 359/391 |
| 4,477,157 | 10/1984 | Gaul | 359/394 |
| 4,589,741 | 5/1986 | Clegg | 359/394 |
| 4,679,914 | 7/1987 | Rosenberg | 359/396 |
| 4,680,469 | 7/1987 | Nomura et al. | 250/311 |
| 4,764,342 | 8/1988 | Kelln et al. | 356/246 |
| 4,836,667 | 6/1989 | Ozeki | 359/393 |
| 4,985,206 | 1/1991 | Bowman et al. | 422/99 |
| 5,038,035 | 8/1991 | Nishimura et al. | 250/311 |
| 5,089,315 | 2/1992 | Rosenberg | 428/192 |
| 5,219,526 | 6/1993 | Long | 422/102 |

Primary Examiner—Loha Ben
Assistant Examiner—Thong Nguyen
Attorney, Agent, or Firm—Pravel, Hewitt, Kimball & Krieger

[57] ABSTRACT

A microscope slide stage for holding a plurality of slides in a plane for sequential viewing by any slide viewer, the stage including a plurality of slide slots have associated with each slot a slidable wedging clamp for securing slides on the stage. The slide stage is particularly suitable for use with computerized slide mapping and analyzing devices.

22 Claims, 3 Drawing Sheets

MICROSCOPE SLIDE ROTARY STAGE

FIELD OF THE INVENTION

This invention relates to a microscope slide stage capable of sequentially moving a series of slides into alignment with a slide viewing device.

BACKGROUND OF THE INVENTION

Automated systems for analysis of glass slide specimens using optical or electron microscopes have been available for a number of years. For example, U.S. Pat. No. 5,038,035 to Nishimura is directed to such an automated analyzing/processing apparatus, which includes a computer controlled stage for positioning a single slide in a desired position relative to a microscope optic. Another example of a computer controlled stage can be found in U.S. Pat. No. 4,122,518 to Castleman et al. Such stages to date have been designed to accommodate only one slide at a time, thereby requiring either a human or robotic loading and unloading mechanism for placing each slide in alignment for viewing and analysis. The loading and unloading operation between analysis of each slide is time consuming, and involves an additional risk of breaking slides. For example, an automatic slide loading and unloading mechanism has been marketed by PSI, Inc. as part of its automatic metaphase finder system. This mechanism includes a vacuum system and mechanical arms for lifting a slide from a vertical position in a slide cartridge to a horizontal position on a single slide stage, where a second vacuum system holds the slide to the stage. Another mechanical system then moves the stage to a first locating point and then a second locating point, and then to a position for focusing beneath the viewing lens of the system.

This system is designed to permit sequential analysis of a group of up to sixty slides by the computer controlled system, without attendance by an operator. Although generally acceptable for this purpose, mislocation of a slide during the vacuum pick up and robot arm rotation to horizontal can cause the system to jam if the arm misses the slide during the pick-up operation or misses the slide cartridge slot during the replacement operation. When such misses occur, one or more slides may break and the sequencing and analysis operation is then stalled until an operator attends to the equipment and restarts the operation.

For clinical cytogenetics purposes of identifying and mapping chromosome spreads on a prepared specimen slide, and in particular, for use with a digital karyotype image system such as described in U.S. Pat. No. 4,122,518, it is important to locate the slide accurately relative to the viewing and mapping device. For example, the sixty slide cartridge system described above, for loading and unloading slides in a sequence, requires a first calibration step using a calibration slide for the loaded tray, and then individual slide location calibration between each slide after they are vacuum secured to the single slide tray. Therefore, for single slide stages, each slide position must be calibrated using at least two additional mechanical stops coupled to the computerized system.

It would therefore be desirable to provide a microscope slide stage that can be loaded with multiple slides at once, so that the analysis of all slides can be accomplished in sequence, without interruption of the computer analysis process, or the need to man the machine during the analysis process. It would also be desirable to provide a system for sequencing slides through the analyzer which does not involve the significant risk of breakage inherent in systems which require mechanical movement of the slides once they are loaded for sequenced analysis. Finally, it would be desirable to be able to reference multiple slides to a single fixed location on the slide stage to avoid the need to calibrate the location of each individual slide relative to the slide viewer before analyzing or mapping the slide's image.

SUMMARY OF THE INVENTION

In its broadest sense, the invention includes a slide stage having formed therein a slide slot for supporting a microscope slide, and a wedge for holding the slide in a fixed location within its slot. The invention permits a plurality of slide slots to be located on a single slide stage with a wedge shaped clamp associated with each slot for securing each slide thereon. The invention utilizes frictional forces provided by the wedge shaped clamp in cooperation with the slot slide for forcing a slide into abutment with a slide slot side and end boundary and a slide supporting surface.

DETAILED DESCRIPTION OF THE PREFERRED EMBODIMENTS

Figure 1:
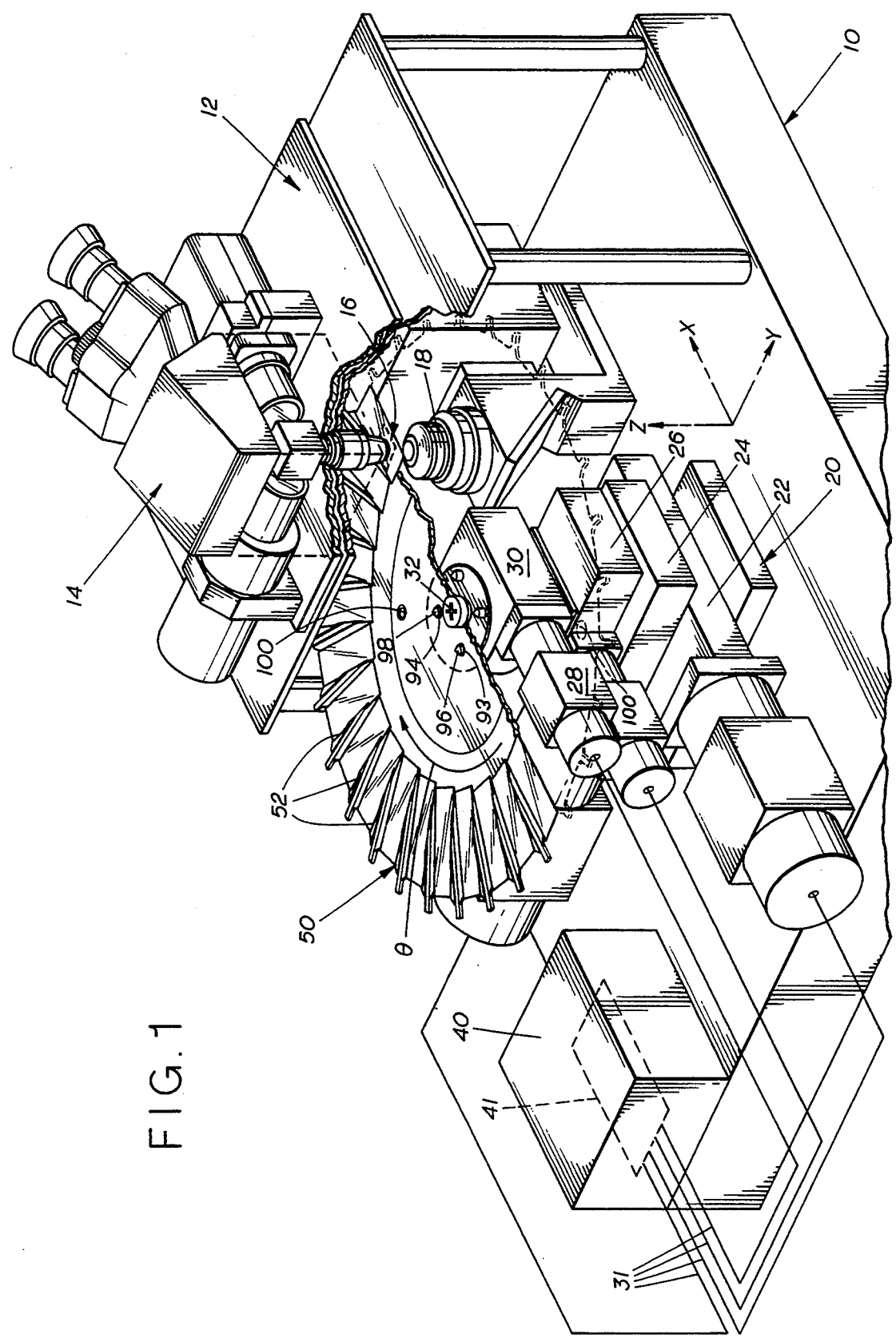
FIG. 1 is a perspective view of a preferred embodiment of the rotary stage of the instant invention, shown mounted with a viewing device on a single platform.

FIG. 1 illustrates the features of the invention in the context of an optical bench 10 having mounted thereon a microscope platform 12, which in turn mounts a microscope 14 in position for viewing a slide through a viewing window 16. Beneath the viewing window is an illumination device 18. For computerized slide analysis, the platform 12 also mounts a line scanner S and a video camera V, as well as the microscope viewer or eyepiece E.

Figure 2:
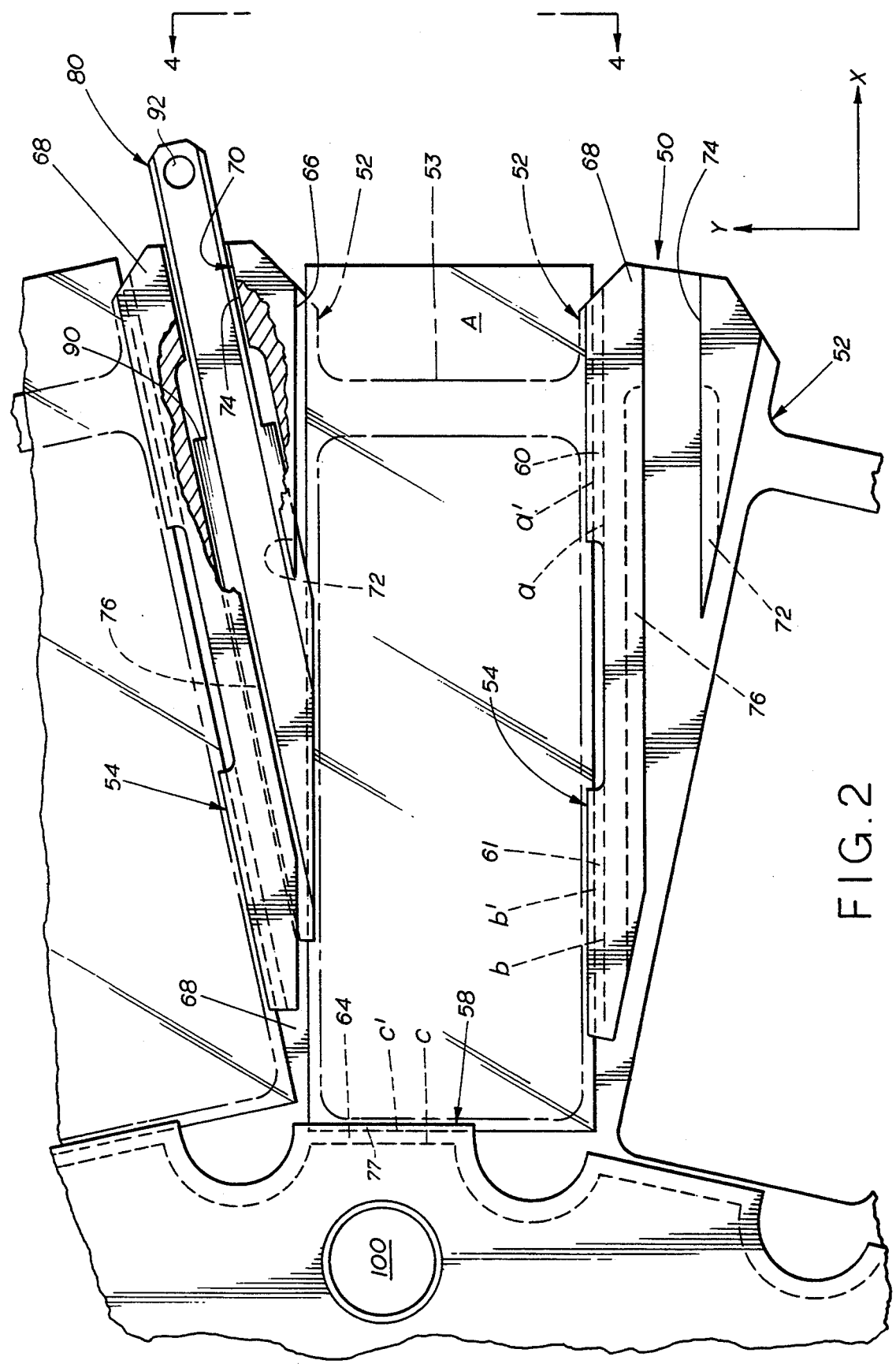
FIG. 2 is an exploded plan view of the rotary stage embodiment of FIG. 1, illustrating a slide secured in place on a slide slot with a removable clamp in accordance with the invention.
Figure 3:
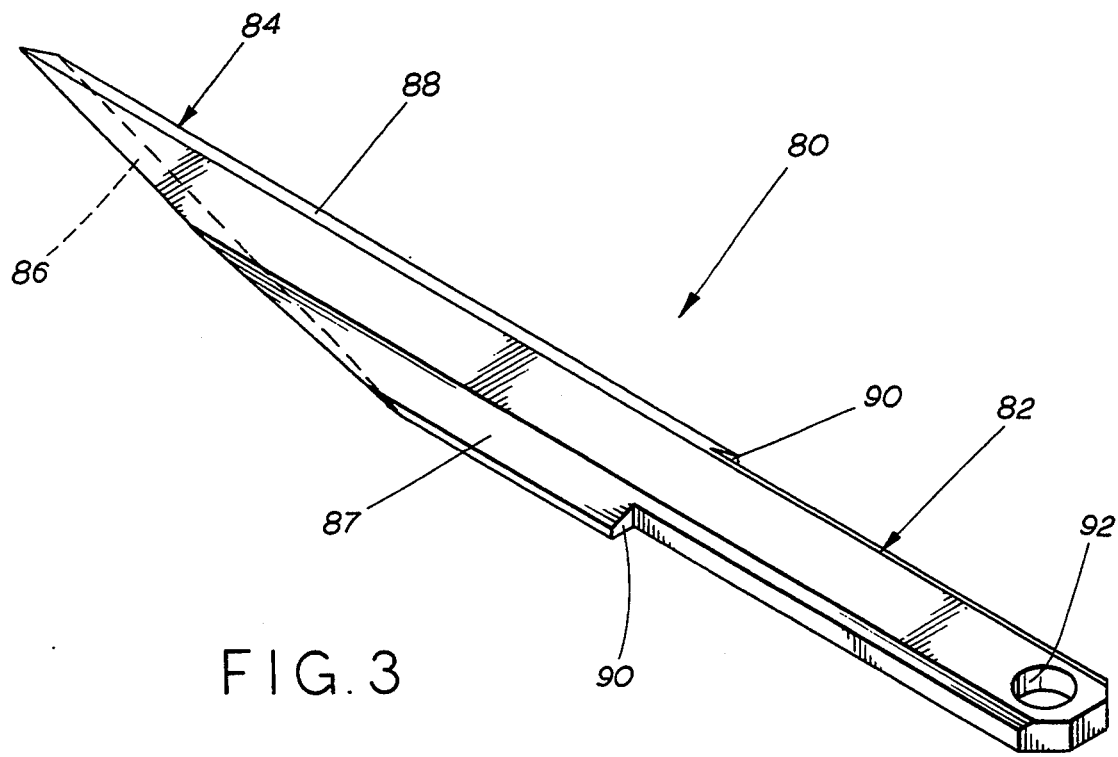
FIG. 3 is a perspective view showing in detail a preferred embodiment of the removable slide clamp of FIG. 2.
Figure 4:
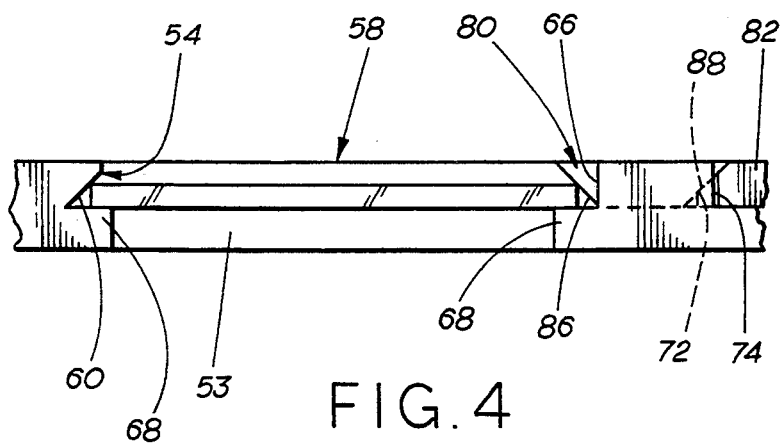
FIG. 4 is an end view along line 4—4 of FIG. 2, showing the slide clamp of FIG. 3 in position securing a slide in a stage slide slot.

A preferred embodiment of a rotary slide stage 50 of the instant invention is shown in FIG. 1 in this context, and in more detail in FIG. 2, with the slide clamp feature of the invention illustrated in detail in FIGS. 3 and 4.

Slide Stage Moving Mechanism

In the embodiment of the invention shown in FIGS. 1 and 2, as practiced, the slide stage 50 is mounted for movement by a slide stage moving mechanism 20, which includes a series of motor driven stages. Beginning at the bottom of the series, as shown, a first translation stage 22 permits movement of the slide stage in one linear direction, e.g. along the X axis as shown in FIG. 1. A second translation stage 24 permits movement of the slide stage in a second linear direction, e.g. along the Y axis, and a third translation stage 26 permits movement of the slide stage along the Z axis. Movement in the X and Y directions permits a slide mounted on the stage to be moved into alignment with the microscope viewing window 16. Movement in the Z direction permits the mounted slide to be brought into focus for viewing by the microscope 14.

Operatively connected to each of the translation stages 22, 24, and 26 and with the rotation platform 30 is a stepping motor, such as the stepping motor labeled 28 in FIG. 1, which is associated with the rotation platform 30. The stepping motors 28 provide for stepwise movement of the stage in each of the X, Y, Z, and $\theta$ directions. The step-wise movement permits individual slides mounted on the stage to be moved into alignment, sequentially, with the view window. Motor drive 40 is connected to each of the translation stages 22, 24, and 26, and to the rotation platform 30 by way of the stepping motors 28 by leads 31.

The motor drive 40 includes computer control means 41 for stepwise movement of the stages in their X, Y, Z, $\theta$ directions, which, in conjunction with additional software (discussed below) can control the slide stage moving mechanism 20 for movement of the rotary slide stage 50 to any position within the mechanical limits of the translation stages 22, 24, and 26. As practiced, each of the translation stages 22, 24, and 26 and the rotation platform 30 and the motor drive 40 with its associated computer control means 41 are standard items commercially available from Klinger Scientific. However, any commercially available motorized moving means could be used. As will be appreciated in light of the discussion below relating to slide stage calibration, the rotary slide stage embodiment of the present invention is most advantageously used in conjunction with an integrated computer system for coordinating the stage movement with the slide analysis program.

Slide Stage

Turning now to the specific features of the rotary stage 50, the stage is generally circular and includes a plurality of slide slots 52 spaced about its periphery. Each slide slot 52 includes a peripheral slide supporting surface area having an opening therein sized to correspond with the specimen-containing, scanning area of a standard 75 mm×25 mm×1 to 2 mm glass microscope slide. An additional crosswise supporting surface 53 is conveniently provided for supporting the slide adjacent a slide label/handling area generally designated as "A" in FIG. 2. It has been found that a peripheral supporting surface area of approximately 1½ mm in width provides adequate support for a standard glass slide, while maximizing the area available for scanning the specimen-containing area of the slide.

The slide supporting surface area is bordered on a first long side by edge 54, having formed therein a first dovetail groove portion 60 adjacent the periphery of the stage 50 and a second dovetail groove portion 61 adjacent the internal end of the long side edge 54. Although a continuous groove of any configuration could be used, the separate dovetail groove portions 60 and 61 provide two pairs of positive slide locating points (illustrated as a and a' and b and b' in FIG. 2) even if the slide side edge is distorted somewhat from a straight line and/or from a truly perpendicular side edge. The slide supporting surface further includes an internal edge or boundary 58, also having formed therein a dovetail groove portion 64 sized to be slightly shorter than the short slide end supporting surface. Again, although any groove configuration or length is acceptable, this shortened dovetail groove portion 64 provides another pair of positive locating points (illustrated as c and c' in FIG. 2) even if the slide end edge is distorted.

The second long side of the slide slot 52 includes additional slide supporting surfaces bordered by a straight side edge 66 adjacent the peripheral portion of the slide slot 52. It is not necessary to include a groove in the edge 66 and the straight edge makes it easy to insert and remove a slide from its slot by merely dropping it onto is slide supporting surface area.

Between the straight edge 66 and the slot's internal edge or boundary 58 is a slide clamp supporting surface 68. The clamp supporting surface 68 is bordered on one side (e.g. the left or bottom side as shown in FIG. 2) by a first clamp slot edge 70 having a first clamp-guiding dovetail groove 72, and a straight edge portion 74. For the circular slide configuration shown in the drawing, the edge 70 is conveniently disposed on the backside of the fourth slide edge containing the slide-guiding, slide slot straight side edge 66. The slide clamp supporting surface 68 is bordered on its opposing long side by a second clamp-guiding dovetail groove 76. These grooves 72 and 76, together with the straight edge 74, are designed to cooperate with the clamp embodiment shown in detail in FIG. 3, and discussed below. The second clamp-guiding dovetail groove 76 and first clamp slot edge 70 are spaced from one another on an unbounded surface area which encompasses the central portion of the slide slot 52. As will be understood in light of the following discussion of the configuration of the preferred embodiment of slide clamp 80, the straight edge portion 74 on the short edge of the clamp supporting surface 68 enables the slide clamp to be captured within and on its supporting surface 68.

Slide Clamping Mechanism

Turning now to the features of the slide clamp 80, shown in detail in FIG. 3, as practiced, the clamp 80 is generally a sword-like configuration, including a handle portion 82 and wedge portion 84. The wedge portion 84 includes a first lower surface bevel 86 for frictionally engaging an upper surface of a slide. The remaining edges of the slide clamp are beveled on their upper surfaces, trailing upper bevel 87 for gliding within the first clamp-guiding dovetail groove 72 and leading upper bevel 88 for gliding within second clamp-guiding dovetail groove 76. Both bevels are designed to cooperate with their respective dovetail grooves to permit the clamp to wedge a slide into position in abutment with the slide slot boundaries provided by the slide slot dovetail grooves 60, 61, and 64. The spacing between the edge 70 and the grooved edge 77 permits the lower surface bevel 86 to contact a slide in its mid portion and move it within the slide slot 52 into positive contact with the locating points within the grooves 60 (a and a'), 61 (b and b'), and 64 (c and c').

In particular, when a slide is resting within the slide slot 52, pushing the clamp 80 radially inwardly exerts frictional forces on the slide downward and diagonally to move it into engagement with its slot supporting surface and toward the first long slide slot side edge 54 (at the top of FIG. 2) and toward the short, slide slot's internal edge or boundary 58. These forces move the slide side edges into positive contact with the dovetail grooves 60, 61 and 64 at pairs of locating points, illustrated in FIG. 2 as the points a and a' in the groove 60, b and b' in the groove 61 and c and c' in the groove 64.

The clamp handle portion 82 also includes a ledge 90 which acts as a stop against the clamp slot straight edge portion 74 so that the clamp 80 cannot be pulled out of the stage 50 when pulled along its supporting surface 68, as illustrated in the cutaway portion of FIG. 2 surrounding the ledge 90. A hole 92 is conveniently formed in the handle portion 82 for ease in gripping the handle to move the clamp within its guiding dovetail grooves 72 and 76 along its supporting surface 68.

As can now be appreciated, the slide slot and clamp design can be used to form a stage of any dimension to hold any number of slides for sequential viewing by the microscope 14. As practiced, the rotary stage 50 was designed to hold thirty slides on a generally circular stage having a diameter of about 400 mm. The slide slots were spaced about the periphery of the stage 50, with the centerline of each slide slot 52 offset relative to a radius of the stage. This offset was provided so that the stage can be used with a stage movement mechanism adapted for movement of each slide in a continuous combination of linear and radial sweep across its surface.

With the above described slide slot and clamp arrangement, the slides can be loaded onto the stage before or after the stage is mounted on its moving mechanism 20. Each slide is placed on its slide supporting surface and manually positioned generally against the internal slide slot boundary 58. Thereafter, the clamp 80 is moved on its supporting surface 68 until it is wedged between its clamp-guiding dovetail grooves 72 and 76, with its first lower surface bevel 86 firmly frictionally engaging the top surface of the slide. From one to thirty slide slots can be loaded with slides ready for unattended viewing and analysis by the microscope 14. Slides can be easily removed after analysis by sliding the clamp 80 outwardly until the slide is released from the frictional forces exerted by the clamp, conveniently limited by the stop provided by the ledge 90 hitting the straight edge 74. With the slide released, it can be easily removed from its slot by either sliding it outwardly along its supporting surface or lifting it off of the surface, preferably using the slide handling or label area "A".

Returning to FIG. 1, after the slides are mounted, the slide stage 50 can be conveniently mounted on the rotation platform 30 by placing first locating holes 93 and 94 on the slide stage 50 over pins 96 and 98 respectively, on the rotation platform 30. The stage 50 is then secured to the platform by way of the mounting screw 32. The platform pins and stage holes permit the stage to be positioned on the platform so that step wise rotation of the rotation platform 30 positions each slide slot sequentially in general alignment with the microscope viewing window 16. With this arrangement, after the slide stage 50 is securely mounted to the rotation platform 30, it can be calibrated using calibration targets 100 on stage 50, discussed in more detail below.

Although the slide stage may be formed of any material, for durability, to minimize damage from repeated insertion of glass slides in the dovetail grooves, as practiced, the stage was formed of anodized aluminum with hard-anodized indexing surfaces (i.e. grooves 60, 61, and 64) for wear resistance. Similarly, although the slide clamp 80 may be formed of any material capable of being formed with some bevels, it is preferred that the clamp material be somewhat flexible and resilient, e.g., moldable or machinable plastic, so that the clamps can be bent somewhat for insertion within their slots (with the slide slot empty) and yet will stay within the boundary formed by the stop formed by the handle ledge 90.

As can now be appreciated, the rotary slide stage and clamp of the instant invention includes many design features that are not limiting to the invention. For example, forming the slide clamp of a compliant material coupled with provision of a clamp stop minimizes the problem of lost slide clamps, but is not necessary to the practice of the invention. Similarly, the clamp edge and slot groove configurations can be any type of V guide or wedge guide known to one of ordinary skill in mechanics in keeping with their function of slidably engaging the edges of the clamp supporting surface and frictionally engaging a microscope slide.

Computer Control of Stage Movement for Slide Mapping

The type of computer instructions to translate the stepwise movement provided by the motor drive 40 into X, Y, Z, and $\theta$ slide mapping coordinates depends on the particular motor drive and its associated computer control, as well as the particular high level command instruction given by the mapping software. The following instructions were developed for use with the motor drive and controls of the type sold by Klinger Scientific, and the automatic metaphase finder or mapping device marketed by PSI, Inc.:

Move the X-axis the specified number of steps;
Move the Y-axis the specified number of steps;
Move the X- and Y-stages the specified number of steps simultaneously;
Move the Z-axis (vertical) the specified number of steps;
Move the $\theta$-axis (rotation) the specified number of steps;
Read the status of all limit switches;
Initialize the stage assembly and move all axes to their origin positions;
Move the X- and Y-stages to their origin positions;
Move the Z-axis stage to its origin position;
Move the $\theta$-axis stage to its origin position;
Move the X- and Y-axis stages to a specified absolute position;
Move the Z-axis stage to a specified absolute position; and
Move the $\theta$-axis stage to a specified absolute position.

These instructions would be generally applicable for directing a programmable motor drive to move an object mounted for movement in all directions in step-wise fashion using translation stages, a rotation platform, and stepping motors.

The computer control of the motor drive 40 in conjunction with the calibration targets 100 provides the capability of calibrating a particular slide stage and motor drive assembly relative to a fixed viewing position, and to calibrate individual slide stages for use with the complete motor drive and viewing platform assembly.

Slide Stage Calibration and Mapping

The above described embodiment of the invention lends itself to convenient and accurate factory calibration of the stage and its associated moving mechanism mounted on a single platform. Factory calibration involves mounting a slide stage on the motor assembly and then using the motor assembly to place calibration targets 100 in line with the viewing window 16, and in focus for the microscope 14 or other viewing device.

The targets can include any suitable fiducial mark such as cross hairs, a corner mark, lines or bars or the like. The position reading for each target, together with the known distance between them, provides X, Y, Z, θ stage reference coordinates. With a standard calibration slide in each slide slot, a target reference point on the calibration slide is aligned with the viewing window 16. Its X, Y, Z, θ coordinates are then read by the low level software to provide an absolute position relative to the X, Y, Z, θ stage coordinates determined from the stage's target references. The absolute reference coordinate position for each calibration slide can be stored in the motor control software in connection with a slide slot number label and a particular unique slide stage serial number. With this calibration technique, the end user need not perform any calibration of individual slide slots, but need only input the slide stage serial number and rely on the stored data which provides the reference information for converting a position data point on a specimen slide to an absolute position on the slide for accurate specimen slide mapping.

As can now be appreciated, because the slide stage design, with its clamping mechanism, provides for repeatable, accurate positioning of specimen slides relative to its supporting slide slot, factory calibration is possible, and the stage slots and their locations relative to one another on the stage are not required to meet the exacting manufacturing tolerances that would otherwise be necessary. If the end user removes the tray that was initially factory mounted and calibrated, and replaces it with another factory calibrated tray, calibration involves only establishing the initial coordinate references for the tray by following the procedure of reading the coordinates of the tray calibration targets 100. With this base reference, the factory calibration data provided with the tray can be input or retrieved from the motor control's memory to provide the data for taking absolute position readings from each specimen slide loaded on that particular tray.

An alternative to using individual calibration slides and factory calibration of the slide slots is for the end user to mount specimens on blank slides that include inscribed calibration target markers. With this technique, the software can be programmed to recognize and read the coordinates of the inscribed target marker on each specimen slide and use that markers' coordinates in conjunction with the coordinates of the calibration targets 100 as the fixed reference for mapping the entire specimen slide.

Slide Stage Suitable for Both Automated and Manual Slide Analysis

As can further now be appreciated, although the detailed description relates to an embodiment of the invention particularly adapted for use with a computerized slide analysis system, the stage and wedging clamp are suitable for use for any type of slide analysis. With a simple mechanical indexing mechanism, an operator can still load a plurality of slides on the stage and then manually index them past a viewing optic for visual analysis, with the following advantages flowing from the basic concept of the invention.

For example, the stage itself, without any associated moving mechanism, eliminates slide handling once the stage is loaded, and permits use in any orientation, e.g. vertically as well as horizontally. The stage can be configured to provide space for any number of slides, limited only by practical handling and mechanical indexing constraints. The slide slot design provides for kinematic locating of each slide in all six degrees of freedom by the locating points and locking wedge, which is useful with or without a computerized analysis system. Slide loading and unloading is simple, and requires no special operator skills. Elimination of individual slide calibration greatly reduces the time consumed in analyzing a series of slides. The dovetail groove design can accommodate slides of various thicknesses without modification. The calibration targets provide definition of stage reference coordinates. Each slide slot can be numbered for quick slide reference.

Additional features of the embodiment described in detail above make the rotary stage particularly well suited for use with automated chromosome analyzers but are not essential for practicing the invention. For example, the combination of a circular stage and radially offset slide slots permits automated slide scanning by moving the slide stage in a continuous, sweeping pattern to scan the entire viewing area of a slide, which may be more efficient than a step wise X and Y scan provided by the above described motorized translational stages. The calibration markers or windows are another example of the described embodiment being adapted for use with a computerized analysis device. The particularly described slide slot dovetail grooves and their associated locating points a, a′, b, b′, c, and c′ are designed to accommodate slides of varying thickness and at the same time provide accurate indexing of each slide once it is securely mounted on its slide slot by way of its associated slide clamp. However, any V guide or wedge guide arrangement can be used without departing from the spirit of the invention. The described slide stage also provides for unobstructed visibility of the slide identification area at the periphery of the stage. The provision of translational movement of the stage permits the identification area as well as the specimen area to be viewed not only with the stage away from the microscope M or other viewing device but also through the viewing window 16. Various modifications of the above-described embodiment can be made without departing from the spirit of the invention, the scope of which is defined by the claims which follow.

What is claimed is:

1. A slide stage for securing a plurality of slides on a single slide viewing platform comprising:
    a base defining at least two slide slots for supporting at least one slide having a first slide edge and a second slide edge, and further defining a wedge slot between the slide slots wherein each slide slot includes a first locating edge and a second locating edge wherein the first locating edge includes at least two locating points for contacting a point on the first slide edge, and wherein the second locating edge includes at least one additional locating point for contacting a point on the second slide edge, and wherein
    each wedge slot includes a first guiding edge and a second guiding edge for guiding a wedge means therebetween into a wedging position against the slide for securing the slide within one of the slide slots, whereby the slide is in engagement with the slot locating points.

2. The slide stage of claim 1 wherein the wedge means includes a wedge end and a handle end, and wherein the wedge end includes a first side having an undercut beveled edge portion adjacent the handle end and an overcut beveled edge adjacent the wedge end and a second side having a beveled edge portion adjacent the wedge end so that the wedge means is insertable within the first and second guiding edges of the wedge slot for movement from a first position away from a slide positioned in the slide slot to a second secured position with the second overcut beveled edge end resting on the top surface of the slide.

3. The slide stage of claim 1 wherein the slide slots and wedge slot are in substantially the same plane and wherein the wedge slot includes a clamp supporting surface contiguous with a slide supporting surface and wherein the slide supporting surface has an opening therein for viewing a slide specimen mounted by the slide.

4. The slide stage of claim 1 wherein the wedge means is formed of a single piece of compliant material.

5. The slide stage of claim 4 wherein the wedge material is an injection molded plastic.

6. The slide stage of claim 4 wherein the wedge material is a machinable plastic.

7. The slide stage of claim 1 wherein the base, slide slots, and the wedge slot are formed of a single piece of rigid material.

8. The slide stage of claim 7 wherein the rigid material is a metal and wherein at least the first and second locating edges have a hardness comparable to the hardness of glass.

9. The apparatus of claim 8 wherein the metal is aluminum which has been hard anodized to provide the first and second locating edges having the hardness comparable to glass for wear resistance.

10. The slide stage of claim 1 further comprising a viewing means mounted to the viewing platform, and means for moving the base from a first position with the first slide slot in alignment with the field of view of the slide viewing means to a second position with the second slide slot in alignment with the field of view of the viewing means.

11. The slide stage of claim 10 wherein the base has a generally circular top face and wherein the at least two slide slots includes a plurality of slide slots about the periphery of the top face of the base, each pair of slide slots having between them the wedge slot.

12. The slide stage of claim 11 wherein the base includes two, spaced-apart, calibration targets for calibrating the base relative to the field of view of the slide viewing means.

13. The slide stage of claim 11 wherein the base further includes a calibration target for use in adjusting the focus of the viewing means.

14. The slide stage of claim 10 wherein the base moving means comprises a means for rotation of the base about a central axis for sequentially positioning the slide slots in the field of view of the slide viewing means.

15. The slide stage of claim 14 wherein the base moving means further comprises means for translational movement of the base in at least one linear direction in the plane of the base.

16. The slide stage of claim 15 wherein the base moving means further comprises means for translational movement of the base in at least one linear direction perpendicular to the plane of the base.

17. The slide stage of claim 16 further comprising computer control means for controlling the translational moving means.

18. The slide stage of claim 10 wherein the base moving means further comprises computer controllable drive means for operating the base moving means.

19. A method of securing a plurality of slides on a single slide stage comprising the steps of:
Placing at least two slides on a stage base with each of their major surfaces resting on the base within slide slots defined by the base, each of the slide slots having at least three slot edges defining a surface area larger than the surface area of the slide; and
Positioning a wedge in at least one of the slide slots having a slide therein in wedging engagement between at least two of the slide slot edges and the slide.

20. An apparatus for securing a plurality of slides in a single plane, each slide having two major surfaces, for viewing by a microscope objective comprising:
a base having at least two slide slots therein wherein each slot includes a slot surface for supporting one of the major surfaces of the slide, each slot defined by at least three slot edges and having an area defined by the slot edges which is larger than the major surface area of the slide; and
a wedge for insertion into the slide slot to wedge the slide against at least two of the slot edges.

21. An apparatus for sequentially viewing a plurality of slides, each slide having two major surfaces, with each slide being supported by a single slide stage comprising:
a slide stage containing a plurality of slide slots for supporting a plurality of slides beneath one major surface of each slide, wherein each slot includes a frame having three edge portions and a slide supporting surface and wherein the frame is larger than the slides to be viewed; and
a wedge for insertion within at least one slide slot for securing a slide in wedging engagement with the slide slot.

22. An apparatus for securing a plurality of slides in side by side position for sequential viewing by a microscope objective comprising:
a slide stage having at least a first and a second slide slot therein, each slot defined by at least three slot edges and having an area defined by the edges which is larger than the area occupied by a slide;
a first and second wedge for insertion into the first and second slide slots to wedge a first and second slide against at least two of the slot edges;
means for mounting a microscope objective in a fixed position relative to the slide stage;
means for mounting the slide stage for movement into alignment with the fixed microscope objective; and
means for moving the slide stage from a first position wherein a first slide slot is in alignment with the fixed microscope objective to a second position wherein a second slide slot is in alignment with the fixed microscope objective.

* * * * *